United States Patent [19]

Riccitelli et al.

[11] Patent Number: 5,166,990

[45] Date of Patent: Nov. 24, 1992

[54] MULTIPLE OPTICAL FIBER EVENT SENSOR AND METHOD OF MANUFACTURE

[75] Inventors: Samuel D. Riccitelli, Murrieta; Thomas A. Shern, San Diego; Richard Homick, Santee; Alan Nelson, San Diego; Charles S. Bankert, Oceanside; Henry K. Hui, Laguna Niguel, all of Calif.

[73] Assignee: Puritan-Bennett Corporation, Carlsbad, Calif.

[21] Appl. No.: 751,818

[22] Filed: Aug. 29, 1991

Related U.S. Application Data

[63] Continuation-in-part of Ser. No. 565,495, Aug. 10, 1990, Pat. No. 5,054,882.

[51] Int. Cl.[5] ............................................. G02B 23/26
[52] U.S. Cl. ........................................ 385/12; 128/637; 128/692; 385/117; 606/12; 606/15
[58] Field of Search ................. 385/12, 117, 118, 123, 385/141, 147, 902; 606/2, 10-12, 15, 16; 128/637, 692

[56] References Cited

U.S. PATENT DOCUMENTS

| | | | |
|---|---|---|---|
| 4,321,057 | 3/1982 | Buckles | 356/445 X |
| 4,399,099 | 8/1983 | Buckles . | |
| 4,682,895 | 7/1987 | Costello | 385/12 X |
| 4,706,677 | 11/1987 | Goorsky et al. | 128/634 |
| 4,727,730 | 3/1988 | Boiarski et al. | 128/667 |
| 4,749,254 | 6/1988 | Seaver . | |
| 4,752,115 | 6/1988 | Murray, Jr. et al. | 385/12 |
| 4,830,013 | 5/1989 | Maxwell | 128/692 X |
| 4,846,548 | 7/1989 | Klainer | 385/12 |
| 4,865,416 | 9/1989 | Pratt | 385/12 |
| 4,925,268 | 5/1990 | Iyer et al. . | |
| 4,928,694 | 5/1990 | Maxwell | 128/637 |
| 4,954,318 | 9/1990 | Yafuso et al. | 385/147 X |
| 5,000,901 | 3/1991 | Iyer et al. | 385/12 X |
| 5,006,314 | 4/1991 | Gourley et al. | 385/12 X |
| 5,054,882 | 10/1991 | Riccitelli et al. | 385/12 |

FOREIGN PATENT DOCUMENTS

| | | |
|---|---|---|
| 0245073 | 11/1987 | European Pat. Off. . |
| 3038883A1 | 7/1982 | Fed. Rep. of Germany . |
| 2108675A | 5/1983 | United Kingdom . |

OTHER PUBLICATIONS

Mahutte et al, "Progress in the Development of a Fluorescent Intravascular Blood Gas System in Man," *The Journal of Clinical Monitoring,* vol. 6, No. 2, Apr. 1990, pp. 147-157.

*Primary Examiner*—John D. Lee
*Attorney, Agent, or Firm*—Fulwider, Patton, Lee & Utecht

[57] ABSTRACT

The multiple optical fiber event sensor apparatus includes a semipermeable generally cylindrical shaft, one or more optical fiber gas sensor modules within the shaft, and an optical fiber pH sensor module extending beyond the distal end of the shaft, with the sensor modules arranged in an axially staggered relationship. The shaft contains a potting matrix for axially fixing the position of the optical fibers, and includes a gas permeable portion surrounding the one or more gas sensor modules, and a hydrophilic portion covering at least part of the pH sensor module. A hemodynamically shaped, rounded distal end is also provided on the distal end of the shaft. The device provides for a multiplicity of individual sensors incorporated in a single shaft which minimizes cross-interference and thrombus formation when used as an intravascular multi-sensor.

57 Claims, 4 Drawing Sheets

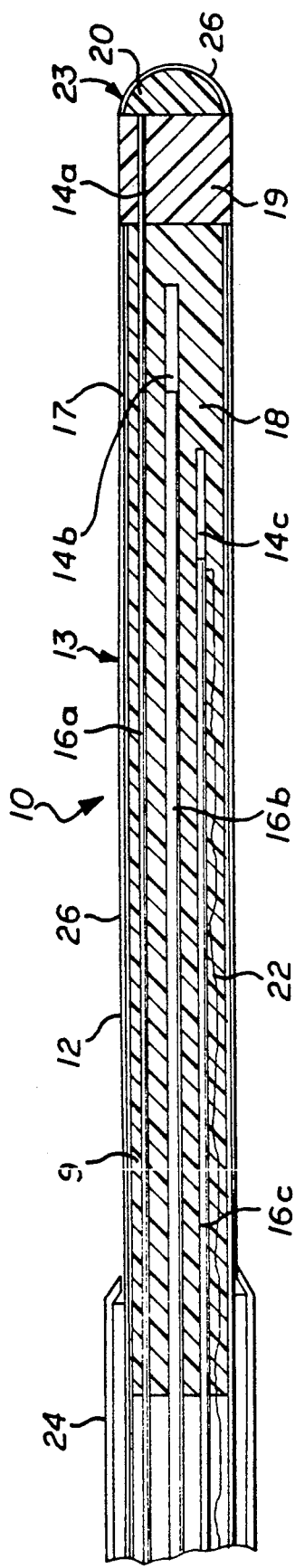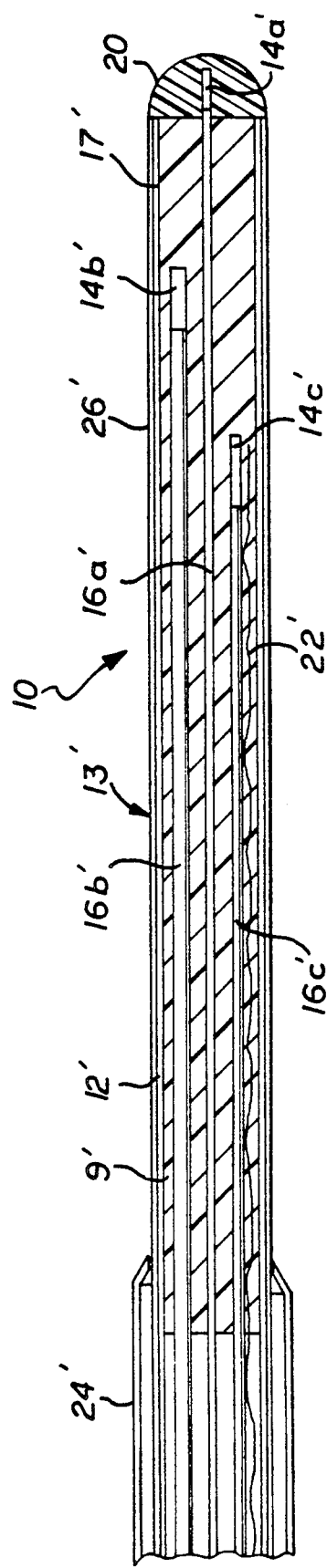

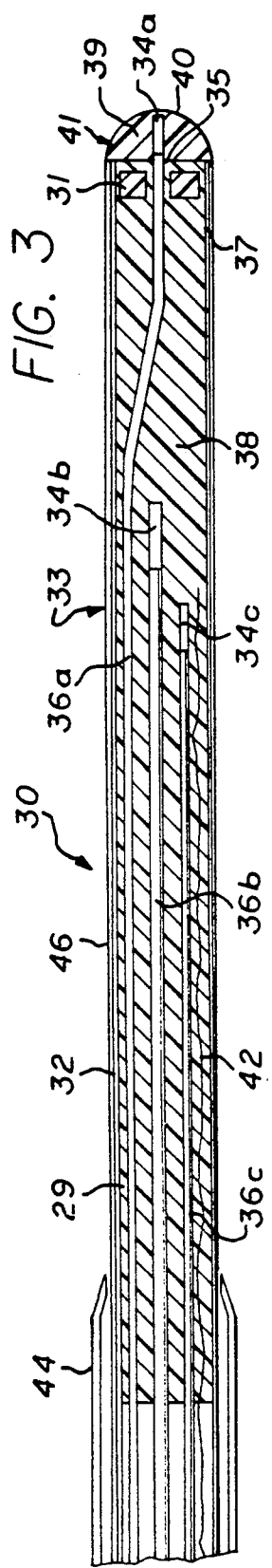
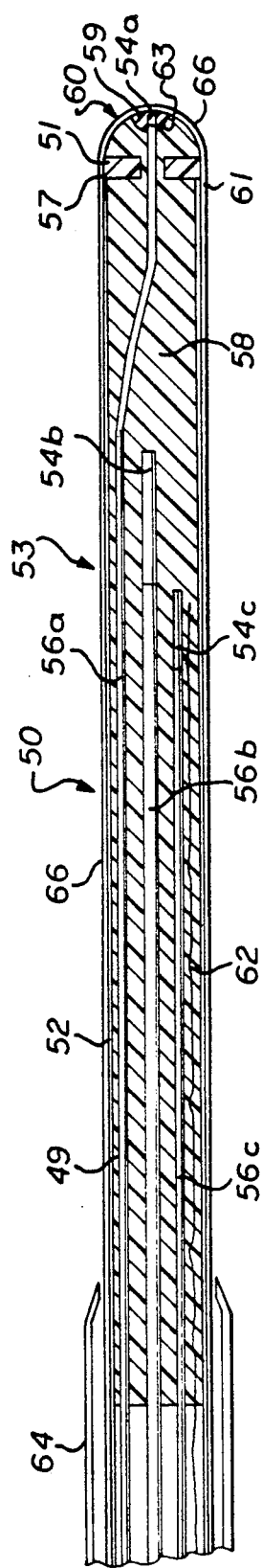
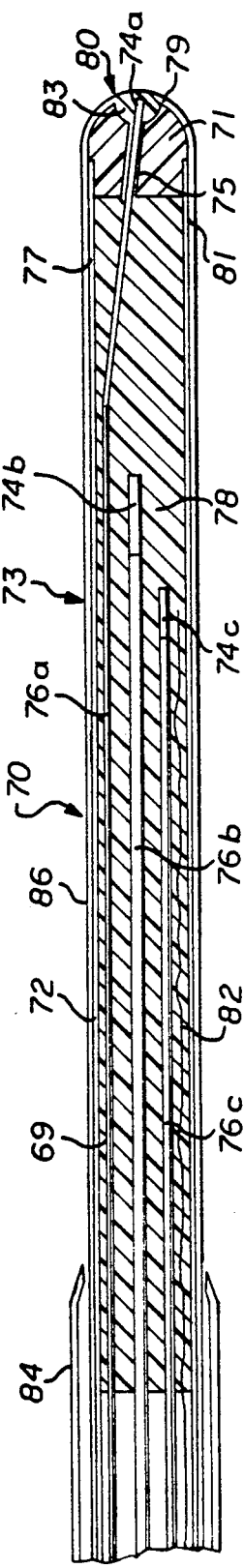

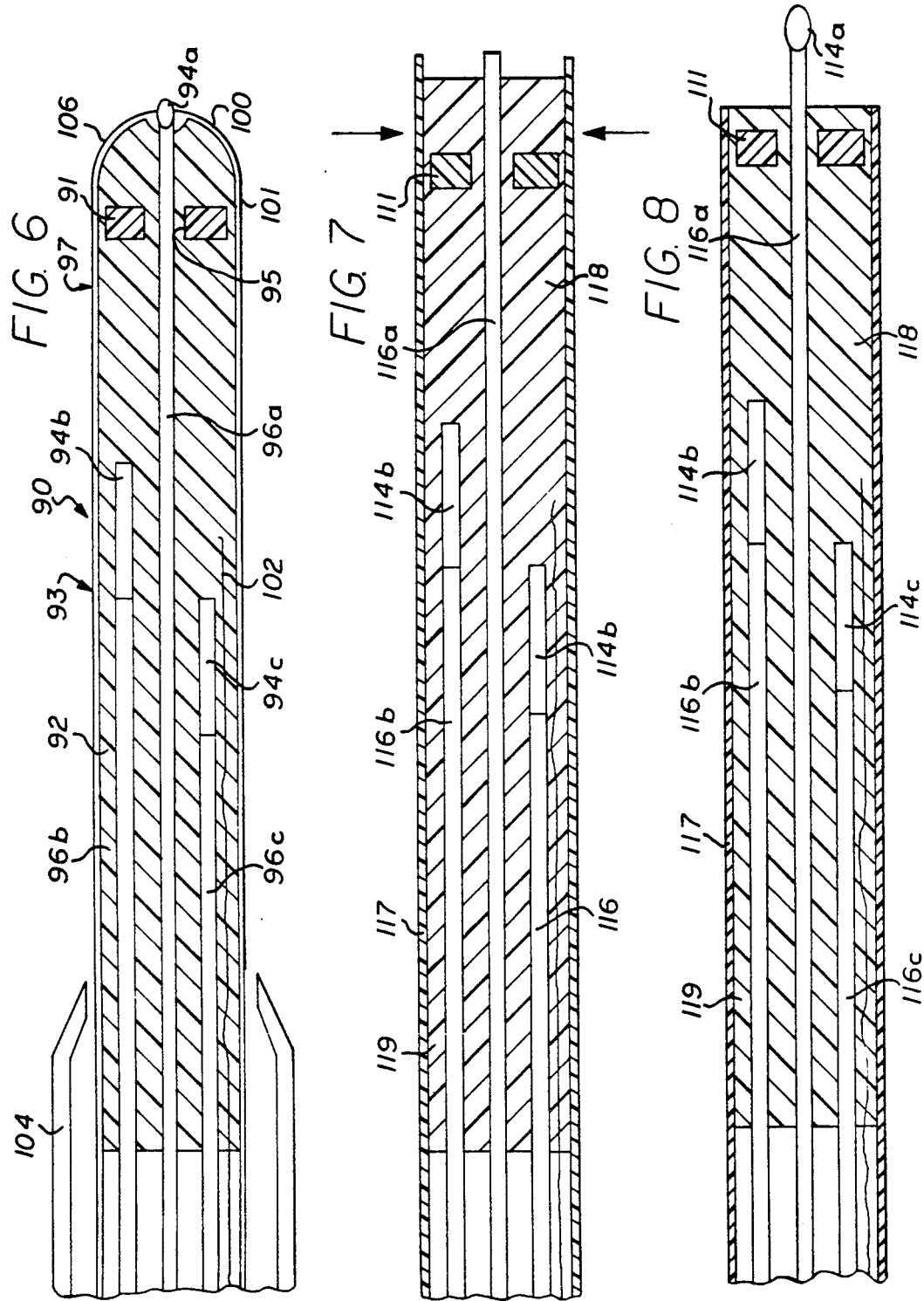

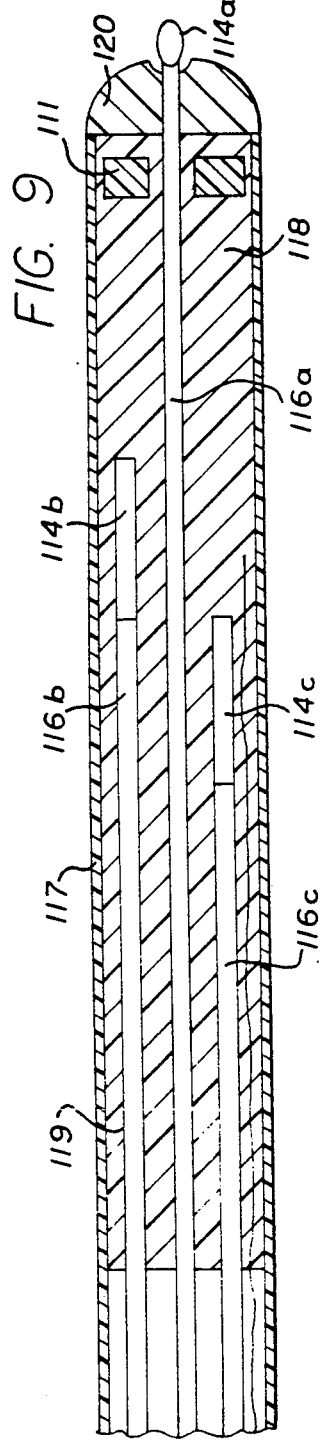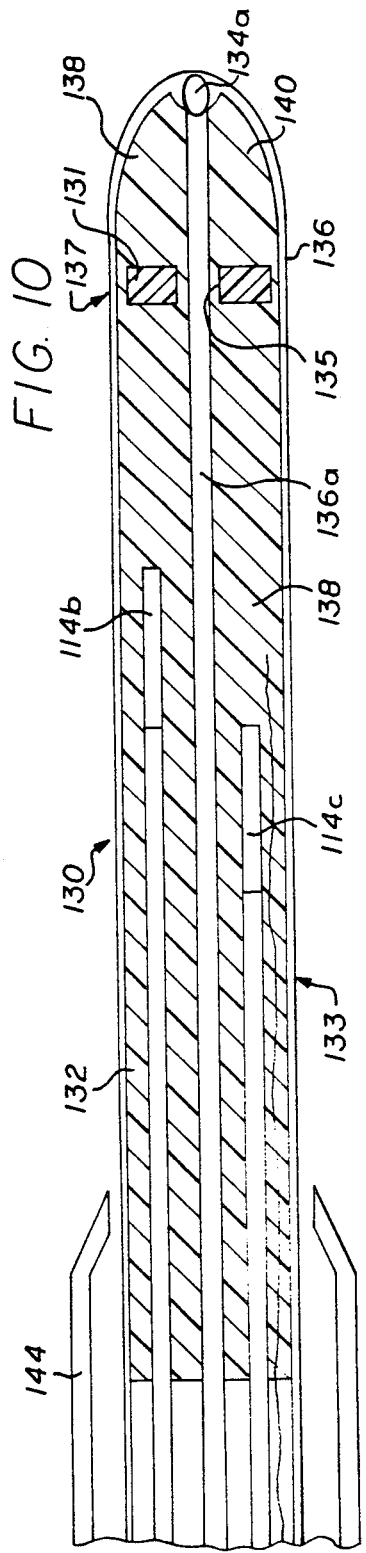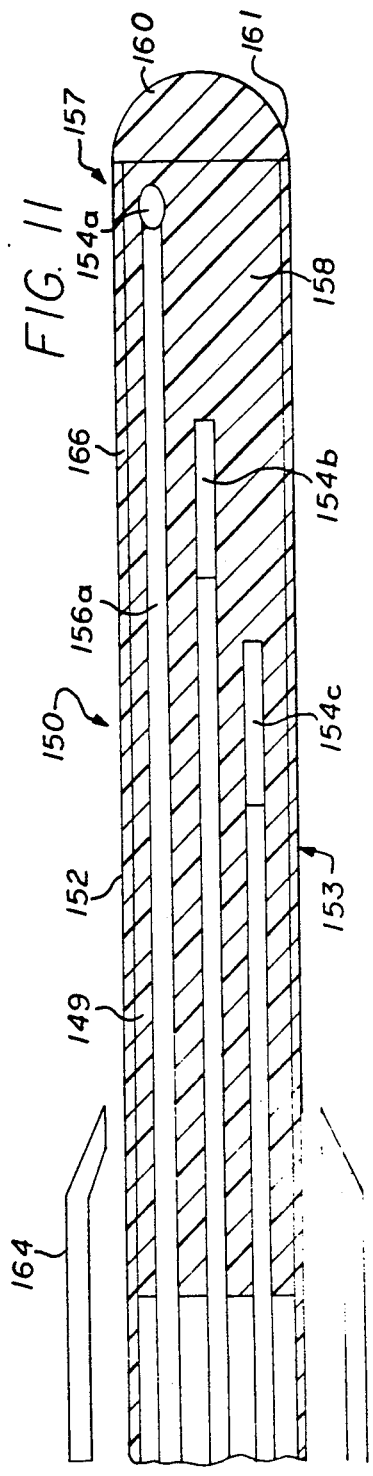

MULTIPLE OPTICAL FIBER EVENT SENSOR AND METHOD OF MANUFACTURE

BACKGROUND OF THE INVENTION

RELATED APPLICATIONS

This is a continuation in part of copending Ser. No. 07/565,495, filed Aug. 10, 1990, now Pat. No. 5,054,882.

1. Field of the Invention

This invention is generally directed to chemical and biochemical analysis for an analyte in a fluid or gaseous mixture. More specifically, this invention concerns a multiple event sensor for performing analysis of multiple analytes and a method of manufacturing the multiple event sensor.

2. Description of Related Art

Measurement of acidity (pH) and the tension or partial pressure of carbon dioxide and oxygen in the blood have become particularly important in modern medicine in determining the respiratory status of a patient. Optical sensors have been developed which are based upon the behavior of the fluorescence reaction of certain dye indicators in the presence of the analyte of interest. The fluorescent indicator is typically immobilized within a permeable membrane on the end of an optical fiber utilized in measuring the intensity of the fluorescence reaction of the indicator at a certain emission wavelength. Another optical fiber may also be used to carry a certain wavelength of light to initiate the fluorescence of the indicator, although it is possible to reduce the size of the sensor by using the same optical fiber for conducting the different wavelengths of fluorescence and excitation light.

Although an optical fiber fluorosensor for oxygen and carbon dioxide has been developed which includes a first indicator layer sensitive to oxygen and a second indicator layer sensitive to carbon dioxide on a single optical fiber, such multiple layer optical fiber sensors can be difficult to manufacture, and there is a concern that such an arrangement of indicator layers may cause cross-interference in one or more of the indicator layers in the sensor. A triple sensor for blood pH, $pCO_2$, and $pO_2$ has also been developed which includes three separate optical fibers having appropriate indicator layers at their ends, but possible cross-interference of the individual sensor layers on ends of the optical fibers remains a matter of concern. Overlap of the ends of the optical fibers which tend to be the thickest portion of the optical fiber sensors can also affect the shape of the sensor, causing an enlargement of the multiple sensor where the sensor regions of the component sensors are placed, which increases the tendency of the sensor to develop thrombus buildup during intravascular use. Where one sensor extends distally beyond other sensors, the placement of the distal sensor can also affect the shape of the distal portion of the sensor, and its thrombogenic properties.

Such optical blood pH sensors also typically perform optimally when embedded in a hydrophilic semipermeable matrix allowing the passage of hydronium ions, while $pCO_2$ and $pO_2$ sensors typically perform best in a hydrophobic, gas permeable matrix. Integrated, multiple sensors thus typically contain the shafts of the component sensors in a bundle, while the analyte sensing regions of the component sensors, contained in the appropriate semi-permeable matrix or membrane, are disposed so as to be individually exposed to the blood, such as in a non-staggered configuration at the distal end of the multiple sensor. In one multiple blood analyte sensing device, the individual sensing regions of component sensors of an integrated sensor bundle are exposed to the sample by windows in the side of the sensor sheath. In another device, individual sensor regions of the different component sensors are not covered with an overcoat, and are together directly exposed to the blood through the side of the device. In yet another device, oxygen and carbon dioxide sensor regions are completely covered in a hydrophobic, silicone matrix, while a pH sensor is only partially covered at a medial portion of the shaft of the device, and is exposed for direct contact with the blood. Such devices typically suffer from an accumulation of blood clots over time, caused by thrombogenicity of the configuration of the sensor windows or exposed sensor regions which offer uneven surfaces that can cause local regions of turbulent blood flow past the sensor. Such devices can also suffer from thrombogenicity due to discontinuities in the chemical composition of the surface of the sensor presented to the bloodstream.

Hence, it would be desirable to provide a multiple blood analyte sensor in which various individual proven sensors are integrated into an apparatus containing the component sensors in a continuous semipermeable matrix having different portions with different permeability characteristics appropriate for each component sensor disposed therein to provide structural integrity and strength. It would be advantageous if such a sensor was in a configuration which minimizes optical cross-interference of individual sensors within the apparatus, and which achieves an overall hemodynamic shape which minimizes turbulence of blood as it flows by the device when it is used intravascularly. It would also be desirable for the sensor to have a surface generally without discontinuities in its chemical properties for improved blood compatibility.

Blood parameter sensor probes can be placed in the blood vessel for a relatively long period of time without otherwise disturbing the patient, thus providing the capability to continuously monitor the patient's blood chemistry. However, with conventional blood sensor probes, a slow heparin flush through an introducer catheter is often required in order to prevent coagulation on the probe, until the probe is removed. It has also been found that the intravascular tissue may possess a different concentration of an analyte, such as oxygen, from that in the moving blood stream. When such a conventional sensor probe is inserted into a patient's vasculature through an introducer catheter, the sensor on the distal tip of the elongated fiber optic probe may be forced into this intravascular endothelial tissue, leading to inaccurate blood gas measurements. On blood gas sensor probe attempts to address this problem by containing the blood gas sensors within an open-ended catheter, the sensors being kept free of blood clots by a slow flow of an anti-clotting solution through the catheter and around the sensor bundle. While this approach may be effective in preventing insertion of the probe into the endothelial wall, a flow of anticoagulant over the sensor can also interfere with the effective operation of the sensor.

It would, therefore, be desirable for a multiple optical fiber sensor to have a non-thrombogenic, hemodynamic configuration which would also allow the sensor to be disposed well into the bloodstream, away from an introducer catheter and the wall of the vascular tissue. Such a sensor could help insure that measurements of a blood analyte of interest are not biased by the local concentration of the analyte in the vascular tissue, otherwise known as the "wall effect", or by the flow of an anticoagulant from an introducing catheter and would help reduce the possibility of injury to the vascular tissue when the sensor was in use for long periods of time.

SUMMARY OF THE INVENTION

Briefly and in general terms, a multiple optical fiber pH and blood gas sensor apparatus according to the present invention includes a generally cylindrical shaft and a distal, generally rounded, hemodynamically shaped end portion to provide the multiple sensor with an overall hemodynamic, non-thrombogenic shape. The body of the shaft substantially comprises a semi-permeable polymeric matrix and a plurality of optical fibers extending through the matrix in the shaft, with each of the optical fibers terminating at their distal ends in an individual sensor module. One or more proximal blood gas sensor modules are preferably disposed within a gas permeable portion of the matrix, and a distal pH sensor module is disposed in a hydrophilic portion of the matrix, which may be near to or project slightly beyond the distal end of the shaft at the naturally occurring stagnation point of blood flow over the multiple sensor. Other sensor modules may be included in the structure to measure physiologic parameters and as temperature or blood pressure. The sensor modules are also preferably arranged in an axially staggered relationship. The polymeric matrix potting materials provide structural integrity and strength for the multiple sensor, and maintain the individual optical fiber sensors in a fixed, axially oriented position.

In one aspect of the invention, the shaft may be constructed to include a sleeve to contain the semi-permeable matrix of the shaft. The sleeve may be formed from a hydrophobic material, and can also be covered with a layer of hydrophilic material, smoothly joined with the exterior surface of a distal hydrophilic portion of the matrix to provide the multiple sensor with a continuous surface with hydrophilic surface energy characteristics for improved compatibility of the multiple sensor with blood. In an alternate embodiment, the sleeve may be formed of gas permeable hydrophilic material which need not be covered with an additional hydrophilic layer. In another embodiment, the shaft can be formed in a mold without an additional sleeve to contain the matrix and optical fibers.

The overall hemodynamic shape of the multiple sensor may advantageously be formed so that the proximal exterior surface of the rounded distal end portion and the adjacent distal portion of the shaft are substantially parallel and concurrent. For purposes of this application, the term "hemodynamic" is intended to mean non-thrombogenic in normal blood flow around the multiple sensor when used intravascularly. In one preferred embodiment, the distal end portion is substantially hemispherical. In an alternate embodiment, the distal end portion can be generally in the shape of a parabola, a tangent ogive or other bullet-shaped configuration. In another embodiment, the distal pH sensor may project slightly from the generally rounded end portion of the sensor, at the naturally occurring stagnation point of the multiple sensor where stagnation of blood flow would normally occur, to allow for maximum sensitivity without substantially detracting from the otherwise hemodynamic shape of the rounded distal end portion. The pH sensor module is typically rounded and may be further covered with a thin portion of hydrophilic material to further smooth the rounded end and fill in any cracks which may occur in the sensor surface, and to preserve the overall hemodynamic shape of the multiple sensor. The generally rounded distal end portion and the smooth junction with the shaft thus provides the multiple sensor with a blood compatible, hemodynamically shaped, non thrombogenic surface, allowing the multiple sensor to be positioned well within the bloodstream for extended periods of time to avoid perturbations in the blood analyte measurements due to local analyte concentrations in the wall of a blood vessel. The rounded distal end also helps to avoid puncturing, or otherwise damaging, the blood vessel wall upon insertion of the multiple sensor. The rounded distal end portion assures that the multiple sensor will not become partially imbedded in vascular tissue, such as the endothelial tissue on the inner wall of an artery, and that the sensor region of the multiple sensor can be disposed within the bloodstream.

In one aspect of the invention, the distal pH sensor is preferably disposed adjacent to the surface of the distal end of the multiple sensor, and is most preferably covered by no more than about 25 microns of hydrophilic material. It has been found that radially centering of the distal optical fiber sensor within the distal end can be advantageous in preparing and maintaining the generally rounded, hemodynamic shape of the distal end of the multiple sensor, such that any distortions or projections of the pH sensor will occur at the normally occurring stagnation point in the flow of blood around the sensor during intravascular use. Thus, in a further preferred embodiment of the multiple sensor of the invention, guide means for radially centering the distally extending optical fiber and associated pH sensor are disposed in the distal portion of the shaft. In one form of the multiple sensor in which the shaft is constructed with a sleeve, the guide means comprises an annular guide ring disposed transversely in the distal end of the sleeve, with a narrow central aperture through which the distal optical fiber sensor extends. In another form of the guide means, the sleeve and annular guide ring are formed together as a unitary structure from the same material. In another embodiment, the guide means comprises a preshaped plug disposed at the distal end of the sleeve, and having a generally central channel through which the distal optical fiber extends, with the distal sensor region being located in a small pocket covered by a thin layer of hydrophilic material.

In one preferred method of making the multiple sensor of the invention, the optical fiber event sensor modules are first threaded into a sleeve, staggered axially within the sleeve with one or more optical fiber gas sensors disposed proximally and an optical fiber for the pH sensor extending most distally. The sleeve is then filled with a polymeric matrix that is permeable to the analytes to be measured. In another preferred method of making the multiple sensor, an annular guide ring is first placed transversely in the distal end of the sleeve for radially centering the distal optical fiber for the pH sensor within a hemodynamically rounded distal end of the multiple sensor. The sleeve is currently preferably formed of gas permeable hydrophobic material, but may also be formed of gas permeable hydrophilic material. When the sleeve is hydrophilic, the distal pH sensor may also be placed within the sleeve. The gas sensors are then potted into place by utilizing a polymeric matrix. The sensor modules which are each mounted on optical fiber are potted into place, with one or more different types of polymeric potting compounds being used to provide the necessary permeability characteristics for each of the individual sensors in the multiple sensor.

In a further preferred aspect of the method of the invention, when the shaft is formed with a hydrophobic surface, the shaft and any portions of the rounded end having a hydrophobic surface may be subjected to a high voltage corona discharge and covered by a layer of hydrophilic material to provide a hydrophilic surface essentially continuous with the hydrophilic region for the pH sensor at the distal end of the multiple sensor. Exposing the sleeve to a high voltage corona discharge is believed to alter the external surface of the sleeve, facilitating better bonding of the hydrophilic layer with the hydrophobic material of the sleeve to provide the multiple sensor with continuous hydrophilic surface energy characteristics.

From the above, it may be seen that the invention provides for multiple individual sensors, which may include a pH sensor and one or more blood gas sensors, incorporated in a single generally cylindrical shaft with a generally rounded, hemodynamically shaped distal end. The sensor system, according to the invention, is easily manufacturable, hemodynamically shaped to avoid thrombogenicity and structurally sound to withstand the rigors of intravascular placement.

Other aspects and advantages of the invention will become apparent from the following detailed description, taken in conjunction with the accompanying drawings, which illustrate, by way of example, the principles of the invention.

BRIEF DESCRIPTION OF THE DRAWINGS

FIG. 1 is an enlarged longitudinal cross-section of one preferred embodiment of the multiple optical fiber event sensor of the invention;

FIG. 2 is an enlarged longitudinal cross-section of a second embodiment of the invention with a distal hydrophilic region;

FIG. 3 is an enlarged longitudinal cross-section of a third embodiment of the invention including a distal guide member;

FIG. 4 is an enlarged longitudinal cross-section of a fourth embodiment of the invention including a distal guide member formed unitarily with the sleeve;

FIG. 5 is an enlarged longitudinal cross-section of a fifth embodiment of the invention showning another form of guide member in the multiple sensor;

FIG. 6 is an enlarged longitudinal cross-section of a sixth embodiment of the invention showing the shaft molded without a sleeve;

FIG. 7 is an enlarged longitudinal cross-section of a first stage of construction of one form of the multiple sensor showing a sleeve filled with a matrix;

FIG. 8 is an enlarged longitudinal cross-section of a second stage of construction of the multiple sensor showing a pH sensing module;

FIG. 9 is an enlarged longitudinal cross-section of a third stage of construction of the multiple sensor showing a rounded distal end portion;

FIG. 10 is an enlarged longitudinal cross-section of a seventh embodiment of the invention with a parabolic distal end; and FIG. 11 is an enlarged longitudinal cross-section of an eighth embodiment of the multiple sensor with the pH sensor located within the sleeve of the shaft.

DETAILED DESCRIPTION OF THE PREFERRED EMBODIMENTS

Problems of structural instability, thrombogenicity, and cross-interference of individual optical fiber fluorosensors have been observed in multiple blood gas sensors. A solution for these modules is provided in the several preferred embodiments of the multiple optical fiber event sensor of the present invention. Specifically, the aspects of fixing the component sensors in axially staggered positions within a tubular sleeve with a semipermeable matrix having variable permeability characteristics appropriate for the component sensor regions disposed therein, forming a hemodynamically shaped, generally rounded tip at the distal end of the tubular sleeve, and covering the sleeve with a hydrophilic layer of material generally continuous with a distal hydrophilic portion have been found to provide important advantages. Construction according to the invention can provide such a multiple sensor with structural integrity, an optimal non-thrombogenic shape and surface for intravascular use, and a minimum of cross-interference among the individual sensors.

As is shown in the drawings which are provided for purposes of illustration, in a first embodiment of the invention, the multiple optical fiber event sensor 10 includes a shaft 9 having a tubular sleeve 12, which is preferably formed of a polymeric material which is permeable to the analyte of interest, and not permeable to blood chemistry which it would be desirable to exclude from the sensor region. The sleeve is preferably formed from a gas permeable polymeric material, which may for example, be a hydrophobic material such as a silicone polymer, having a wall thickness less than about 0.010 inches thick, and preferably less than about 0.002 inches thick. In this embodiment, the silicone sleeve provides a hydrophobic, semipermeable, smooth and blood compatible, generally non-thrombogenic surface 13, and assets in providing structural integrity for the multiple sensor. Other materials which have good mechanical properties, which are gas and/or ion permeable, and which are blood and bio-compatible, may also be suitable. The sleeve may thus also be formed from a gas permeable, hydrophilic polymeric material such as cellulose, or other hydrophilic polymeric materials having appropriate permeability characteristics, depending upon the blood parameters to be measured. A bundle of optical fibers, each typically having a diameter from about 0.125 mm to about 0.225 mm and each having an analyte sensor module at their distal end preferably include a pH sensing module 14a mounted on the distal end of the optical fiber 16a extending through the sleeve with the distal pH sensing module extending beyond the distal end of the sleeve. Blood gas sensing modules 14b and 14c, which may for example be $pCO^2$ and $pO_2$ sensors, may be positioned within the sleeve and mounted on the distal ends of optical fibers 16b and 16c. The sleeve is typically sized approximately 0.65 mm in diameter, with an inside diameter only slightly larger than the diameter of the sensor bundle. The sensor bundle is threaded into the sleeve and the insertion of the sensors may be facilitated by expanding the sleeve by applying a vacuum to the outer surface of the sleeve and/or increasing the internal pressure within the sleeve. Once the sensor bundle has been threaded into the sleeve, the sensor modules on the distal ends of the individual optical fiber sensors are positioned so that they are axially staggered within the sleeve. The sensor modules are preferably axially staggered by sliding the optical fibers such that no one sensor module is directly adjacent to any portion of any other sensor module. This prevents stacking of the active sensor portions, which typically have the thickest diameter of any portion of the optical fiber sensors, since the tip is the region where the chemical indicators are applied. It has been found that it is important to prevent the occurrence of bulges on the surface of the sleeve which may induce turbulent blood flow which can may lead to thrombus formation on the surface of the device when used intravascularly. Staggering the sensors axially in this fashion provides the sleeve with a smooth, cylindrical surface, minimizing the risk of thrombus formation and minimizing cross-talk of fluorescence emissions between the sensors.

Once the bundle of sensors has been threaded into the sleeve and axially staggered within the sleeve, they are potted into place in a distal portion of the sleeve 17 with a semipermeable polymeric potting compound forming a proximal matrix portion 18, which is currently preferably a hydrophobic silicone polymer. The potting material provides structural integrity and strength for the multiple sensor, and maintains the individual optical fiber sensors in a fixed axially oriented position. Other hydrophobic semipermeable materials may also be used. Preferably, the hydrophobic portion of the potting compound should adhere well to the sleeve, should be gas permeable, and should be blood and bio-compatible. The hydrophobic portion of the potting compound may fill all or a portion of the sleeve, but should at least form a proximal matrix portion filling a distal portion of the sleeve surrounding the gas sensor modules and the optical fibers, to fix them axially in position within the sleeve.

To accommodate a pH sensor such as sensor 14a included in the sensor bundle, a distal hydrophilic portion of the semipermeable matrix is formed by a hydrophilic potting compound 19 such as a hydrogel or polyurethane, which is preferably placed on the distal end of the hydrophobic portion of the matrix to form a continuous matrix and to surround the pH sensor module to allow ions from the blood to reach the pH sensor. The hydrophilic portion of the matrix is preferably formed in a rounded shape which has an external proximal surface 21 which is locally parallel and concurrent with the distal exterior portion of the hydrophobic sleeve, to maintain the overall non-thrombogenic, hemodynamic shape of the multiple sensor.

A rounded, and preferably hemispherically shaped end portion 20 is also preferably formed at the distal end of the distal hydrophilic portion of the potting matrix, either after application of the distal hydrophilic portion of the potting matrix, or in the same step as applying the hydrophilic portion of the potting matrix. Other hemodynamic shapes such as tangent ogives, parabolas or the like may also be used for the tip. Although a hydrophobic silicone polymer is a currently preferred tipping compound for this embodiment, the hemodynamically shaped, rounded distal end may be made of the same material used for the hydrophilic portion of the semipermeable potting matrix, and various hydrogens and polyurethanes, or other suitable materials, may also be used in the sensor When a pH sensor is included bundle, the semipermeable matrix forming the rounded distal end of the sensor is preferably at least partially hydrophilic in the region of the pH sensor to facilitate the passage of blood ions to the pH sensor. The semipermeable polymeric matrix used as a tipping compound is shaped to form the hemodynamically rounded tip, preferably having a hemispherical shape at its distal end. The hemodynamic shape requires that the exterior surface 23 of the proximal portion of the rounded distal end be preferably formed to be substantially parallel and concurrent with the exterior surface 13 of the sleeve, and be smoothly joined to the exterior surface of the rounded, distal hydrophilic portion 19, to reduce turbulence of blood flow around the distal end of the multiple sensor. The rounded multiple sensor end thus provides a blood compatible, hemodynamic, nonthrombogenic surface, allowing the multiple sensor apparatus to be positioned well within the bloodstream to avoid the wall effect. The rounded distal end also helps to avoid puncturing, or otherwise damaging, the blood vessel wall upon insertion of the sensor. The tipping compound is preferably applied in a manner so as to avoid the formation of any dead spaces, voids, or bulges in the rounded tip. This configuration has been tested in vivo, in dogs, pigs, baboons, and in humans, with no evidence of thrombus having been observed.

The hemodynamic shape of the multiple sensor allows the distal sensor region to be extended at least 0.5 cm or more beyond the distal opening of the introducer catheter without initiation of clotting, so that the individual optical sensors in the distal sensor region of the multiple sensor are not exposed to interference by anticoagulant solution which may be introduced from the distal end of the introducing catheter or the concentrations of the analytes of interest in the tissue of the inner wall of the blood vessel that are different from those of the bloodstream. In a currently preferred implementation of the invention, an optimum minimum distance for insertion of the distal region of the multiple sensor into the bloodstream has been found to be approximately 3 cm. When the probe is inserted into the vasculature of the patient, this minimum distance has been found to reduce the force with which the sensing catheter will press on the blood vessel wall as it emerges from the distal opening of the introducer catheter and extends along the vascular wall.

Other types of sensors may also be included in the multiple optical fiber sensor, such as a temperature sensor 22, which may be a thermocouple, for example, for measuring patient temperature. The apparatus may be introduced into the vasculature of a patient by an introducer catheter 24, a guiding catheter, or other suitable means. Other types of sensors such as electrodes and pressure sensors may also be incorporated into the multiple optical fiber sensor.

The hydrophobic tubular sleeve and hydrophobic rounded distal end portion may also be covered by a layer of hydrophilic material 26, such as a hydrogel, cellulose, polyurethane, or the like, to provide a continuous external hydrophilic surface for the multiple sensor. When a hydrophobic outer layer is to be used, the hydrophobic material of the sleeve and distal end are preferably first prepared by exposure to a high voltage corona discharge, which alters the external surface of the hydrophobic material, thereby facilitating better bonding of the outer hydrophilic layer with the underlying hydrophobic material. While it is believed that the corona discharge increases the concentration of dipolar entities to a depth of about 1 micrometer on the external surface, the exact mechanism by which bonding is improved is unknown. A hydrophilic external surface can thus be provided for the multiple sensor to insure the absence of transitions in the chemical and/or surface energy characteristics of the surface presented to the blood by the distal hydrophilic portion of the matrix, which may otherwise lead to conformational changes and denaturing of blood proteins. A second embodiment of the multiple optical fiber event sensor similar to that of FIG. 1 is illustrated in FIG. 2. In this embodiment, the multiple optical fiber event sensor 10' also includes a shaft 9' with a tubular sleeve 12', which is preferably formed of a semipermeable polymeric material such as a silicone polymer having a wall less than or equal to about 0.010 inches thick and preferably less than or equal to about 0.002 inches thick. The bundle of analyte sensor modules may include a pH sensor 14a', a $pCO_2$ sensor 14b', and a $pO_2$ sensor 14c', mounted on the distal ends of optical fibers 16a', b', c', respectively, extending through the sleeve. A temperature sensor 22' may also be included in the sensor bundle. The sensor modules are preferably axially staggered as in the first embodiment, except that the pH sensor 14a' extends beyond the hydrophobic potting compound matrix 18', which is also typically a hydrophobic silicone polymer, directly into a hydrophilic polymeric tipping compound matrix 20' which forms the rounded, hemodynamically shaped distal end of the multiple sensor. The hydrophilic polymeric tipping compound 20' in which the pH sensor is embedded may be a hydrogel or polyurethane, for example. The hydrophilic portion 20' is formed in a rounded, and preferably hemispherical shape, to form the distal end of the multiple sensor.

The tubular sleeve of hydrophobic material is also preferably covered by a layer of hydrophilic material 26', such as a hydrogel, cellulose, polyurethane, or the like, to provide a hydrophilic surface substantially continuous with the hydrophilic region at the distal end of the multiple sensor. In order to facilitate bonding of the hydrophilic layer with the hydrophobic material of the sleeve, the sleeve is preferably exposed to a high voltage corona discharge. The sleeve may also be formed from a gas permeable, hydrophilic polymeric material such as cellulose, or other hydrophilic polymeric materials having appropriate permeability characteristics, in which case the additional hydrophilic layer need not be applied over the shaft of the multiple sensor.

The rounded distal end preferably has an external proximal surface 21' which is parallel and concurrent with the distal exterior portion 17' of the hydrophobic sleeve, to maintain the overall nonthrombogenic, hemodynamic shape of the multiple sensor. The shape of the distal end may be formed either after application of the distal hydrophilic portion of the potting matrix, or in the same step as applying the hydrophilic portion of the potting matrix. The exterior surface of the proximal portion of the rounded distal end is preferably formed to be substantially parallel and concurrent with the exterior surface of the sleeve, and is smoothly joined to the exterior surface of the rounded, preferably hemispherical tip, to present a hemodynamic shape to reduce turbulence of blood flow around the distal end of the multiple sensor. The apparatus may be introduced in the vasculature of a patient by an introducer catheter 24', a guiding catheter, or other suitable means.

With reference to FIG. 3, in a third preferred embodiment, the multiple optical fiber event sensor 30 preferably includes a shaft 29 having a tubular sleeve 32 of hydrophobic semipermeable polymeric material such as a silicone. The sleeve preferably has a wall about 0.010 inches or less and preferably about 0.002 inches or less. The multiple sensor includes optical fiber sensor modules, such as a pH sensor 34a, and one or more blood gas sensors, such as $pCO_2$ sensor 34b, and $pO_2$ sensor 34c, mounted on the distal ends of optical fibers 36a, 36b, and 36c, respectively. The multiple sensor may also contain other types of sensors, such as a temperature sensor 42. The sensor modules are preferably axially staggered, with the blood gas sensors disposed in a proximal portion 33 of the sleeve, and the pH sensor extending distally beyond the blood gas sensors. A hydrophobic potting compound matrix 38, preferably silicone, surrounds the gas sensor modules and substantially fills the proximal portion 33 of the sleeve.

An annular guide ring 31, preferably formed from a hydrophobic polymer such as silicone and having a relatively narrow central aperture 35 therethrough, is preferably disposed transversely within the tubular sleeve's distal end 37. The pH sensor 34a extends beyond the proximal hydrophobic potting compound matrix, through the guide ring, and into a hydrophilic polymeric tipping compound matrix 39 disposed over the guide ring, to form a rounded, hemodynamically shaped distal end 40 at the distal end of the multiple sensor. The guide ring thus facilitates radially centering of the pH sensor module within the distal end of the multiple sensor in order to prevent distortion of the hemodynamic shape of the distal end by the pH sensor embedded therein. The hydrophilic polymeric tipping compound in which the pH sensor region is embedded may be a hydrogel, or polyurethane, or the like, for example. While the pH sensor module is preferably covered by a layer of hydrophilic material, the pH sensor module also preferably extends as close as is reasonably possible to the exterior surface of the distal end of the multiple sensor for maximum sensitivity, such that the pH sensor module is preferably covered by no more than about 25 microns of hydrophilic material. The multiple sensor of the invention may be introduced in the vasculature of a patient by suitable means such as an introducer catheter 44, a guiding catheter, or the like.

The hydrophobic tubular sleeve is also preferably covered by a layer of hydrophilic material 46, such as a hydrogel, cellulose, polyurethane, or the like, substantially contiguous with the hydrophilic region at the distal end of the multiple sensor. The external surface of the hydrophobic material of the sleeve is preferably first exposed to a high voltage corona discharge, before the hydrophilic layer is applied over the hydrophobic material of the sleeve. The hydrophilic covering provides the multiple sensor with a substantially continuous external surface with hydrophilic characteristics, thereby improving blood compatibility.

The exterior surface of the proximal portion of the rounded distal end is preferably smoothly joined to the exterior surface of the sleeve to reduce turbulence of blood flow around the distal end of the multiple sensor. The hydrophilic portion of the matrix is also hemodynamically formed in a rounded shape which is preferably hemispherical, so that the external proximal surface 41 of the distal end is parallel to and concurrent with the exterior surface layer 46 at the distal portion of the sleeve 37 to maintain the overall non-thrombogenic shape of the multiple sensor.

A fourth preferred embodiment is illustrated in FIG. 4. The multiple optical fiber event sensor 50 preferably includes a shaft 49 having a tubular sleeve 52 formed of a hydrophobic semipermeable material such as silicone, preferably no more than about 0.010 inches thick, and preferably no more than about 0.002 inches thick. An annular guide ring 51 located transversely within the distal end 57 of the tubular sleeve is preferably formed unitarily with the sleeve, such as by injection molding of the parts together. The guide ring may alternatively be bonded within the distal end of the sleeve, such as by adhesive or heat bonding. The guide ring could alternatively also be secured within the sleeve by a tight friction fit, such as may be accomplished by temporarily expanding the sleeve, inserting the guide ring, and then allowing the sleeve to shrink to retain the guide ring. A relatively narrow central aperture 55 in the guide ring is provided to centrally locate the distal optical fiber pH sensor 54a on optical fiber 56a extending therethrough. Proximally located blood gas sensors, such as $pCO_2$ sensor 54b, and $pO_2$ sensor 54c, mounted on the distal ends of optical fibers 56b, and 56c, respectively, are preferably axially staggered. The sleeve may also contain other types of sensors, such as a temperature sensor 62. A hydrophobic potting compound matrix 58, which is also preferably silicone, substantially fills the proximal portion 53 of the sleeve.

In this embodiment, the hydrophobic polymeric tipping compound matrix 58 is disposed distally over the guide ring to form the rounded, hemodynamically shaped distal end 60 at the distal end of within the multiple sensor. The pH sensor 54a extends through the guide ring to center the pH sensor in the distal portion of the hydrophobic potting compound matrix, in a small pocket or concavity 63 formed at the extreme distal end of the hydrophobic potting compound matrix. The pH sensor and pocket are covered with a hydrophilic polymeric tipping compound 59, to complete the rounded, hemodynamic configuration of the tip. The hydrophilic polymeric tipping compound in which the pH sensor region is embedded may be a hydrogel, or polyurethane, for example. To enhance sensitivity, the amount of hydrophilic material covering the pH sensor is preferably no more than about 25 microns. An introducer catheter 64, guiding catheter, or the like may be used to insert the multiple sensor in the vasculature of a patient.

The external surface of the tubular sleeve and distal hydrophobic portion of the potting matrix may advantageously be covered by a layer of hydrophilic material 66, such as a hydrogel, cellulose, polyurethane, or the like, to provide a substantially continuous hydrophilic surface over the multiple sensor. The sleeve and distal hydrophobic portion of the potting matrix can advantageously both be prepared for bonding with the hydrophilic layer by exposure of the hydrophobic surfaces to a high voltage corona discharge. The distal hydrophobic portion of the matrix and the hydrophilic material at the extreme distal end are formed in a hemodynamically shaped, and preferably hemispherical shape. The external proximal surface 61 of the rounded distal end is parallel to and concurrent with the exterior surface layer 66 at the distal portion of the sleeve 57, to maintain the overall non-thrombogenic shape of the multiple sensor. The external proximal surface of the rounded distal end is smoothly joined in this manner to the exterior surface of the sleeve to reduce turbulence of blood flow around the distal end of the multiple sensor.

In a fifth preferred embodiment, shown in FIG. 5; the multiple optical fiber event sensor 70 preferably includes a shaft 69 containing a tubular sleeve 72. The sleeve is preferably formed of a hydrophobic semipermeable polymeric material such as silicone polymer about 0.010 inches or less thick and preferably about 0.002 inches or less thick. Optical fiber sensor modules, preferably including a pH sensor 74a, and one or more blood gas sensors, such as $pCO_2$ sensor 74b, and $pO_2$ sensor 74c, located at the distal ends of optical fibers 76a, 76b, and 76c, respectively, are preferably axially staggered, with the blood gas sensors being disposed in a proximal portion 73 of the sleeve. The multiple sensor may also contain other types of sensors, such as a temperature sensor 82. A hydrophobic potting compound matrix 78, which is also preferably silicone, substantially fills the proximal portion 73 of the sleeve.

In this embodiment, a preformed, generally cylindrical plug 71, typically formed of a hydrophobic material such as silicone, and having a distal, hemodynamically shaped rounded distal end 80, is preferably disposed in the distal end of the sleeve 77. The plug has a channel 75 extending generally axially through the center of the plug for receiving the distal pH optical fiber sensor, which extends through the channel to the approximate radial center of the extreme distal end of the plug. The pH sensor 74a is preferably disposed in a small pocket or concavity 83 formed at the distal end of the channel, and is covered with a hydrophilic polymeric compound 79, filling the small pocket 83 at the extreme distal end of the multiple sensor to complete the rounded, hemodynamic configuration of the tip. The hydrophilic polymeric tipping compound in which the pH sensor region is embedded may be a hydrogel, or polyurethane, for example. The plug thus facilitates radially centering the pH sensor module within the distal end of the multiple sensor. To enhance sensitivity, the pH sensor is preferably covered by no more than about 25 microns of the hydrophilic material. The apparatus may be introduced in the vasculature of a patient by an introducer catheter 84, a guiding catheter, or other suitable means.

The tubular sleeve and plug may be covered by a layer of hydrophilic material 86, such as a hydrogel, cellulose, polyurethane, or the like, to provide a hydrophilic surface essentially continuous with the hydrophilic region at the distal end of the multiple sensor. The sleeve and distal plug can be prepared for bonding with the hydrophilic layer by exposure of the surface of the hydrophobic materials to a high voltage corona discharge. The distal hydrophobic plug and the hydrophilic material at the extreme distal end of the plug are formed in a hemodynamically rounded, preferably hemispherical shape, with an external proximal surface 81 which is parallel to and concurrent with the exterior surface layer 86 at the distal portion of the sleeve 77, to reduce turbulence of blood flow around the multiple sensor.

With reference to FIG. 6, in a sixth preferred embodiment, the multiple optical fiber event sensor 90 preferably includes a generally cylindrical shaft 92 formed of hydrophobic semipermeable polymeric material such as a silicone. Rather than being formed by use of a sleeve, the sensor is formed in a mold. An annular guide ring 91, typically formed of silicone, is preferably located transversely within the distal end 97 of the shaft. A relatively narrow central aperture 95 in the guide ring is provided to centrally locate the distal optical fiber pH sensor 94a on optical fiber 96a extending therethrough. Proximally located blood gas sensors, such as $pCO_2$ sensor 94b, and $pO_2$ sensor 94c, mounted on the distal ends of optical fibers 96b, and 96c, respectively, are preferably axially staggered. The shaft may also contain other types of sensors, such as a temperature sensor 102. A hydrophobic potting compound matrix 98, which is preferably silicone, substantially comprises the proximal portion 93 of the shaft.

In this embodiment, the hydrophobic polymeric tipping compound matrix 98 is disposed distally over the guide ring to form the rounded, hemodynamically shaped distal end 90 at the distal end of the multiple sensor. The pH sensor optical fiber 96a extends through the guide ring to center the pH sensor in the distal portion of the hydrophobic potting compound matrix, projecting slightly from the rounded distal end portion of the hydrophobic potting compound matrix. The external hydrophobic surface of the shaft, the rounded distal end portion, and a proximal portion of the projecting pH sensor may advantageously be covered by a layer of hydrophilic material 106, such as a hydrogel, cellulose, polyurethane, or the like, to provide a substantially continuous hydrophilic surface over the multiple sensor. The shaft and distal hydrophobic portion of the potting matrix can both be advantageously prepared for bonding with the hydrophilic layer by exposure of the hydrophobic surfaces to a high voltage corona discharge. To enhance sensitivity, the amount of hydrophilic material covering the pH sensor is preferably no more than about 25 microns. An introducer catheter 104, guiding catheter, or the like may be used to insert the multiple sensor in the vasculature of a patient.

The distal end portion of the matrix and the pH sensor projecting slightly from the extreme distal end are both hemodynamically shaped. The external proximal surface 101 of the rounded distal end 100 is parallel to and concurrent with the exterior surface layer 106 at the distal portion of the shaft 97, to maintain the overall non-thrombogenic shape of the multiple sensor to reduce turbulence of blood flow around the distal end of the multiple sensor.

A preferred method of preparing an exemplary multiple sensor will now be described. As is illustrated in FIG. 7, the optical fibers 116b and 116c with blood gas sensors 114b and 114c mounted thereon, respectively, are currently preferably disposed to extend longitudinally in a preferably axially staggered fashion in the sleeve 117. The optical fiber 116a, without the pH sensing module attached, is threaded through the annular guide ring 111 disposed transversely in the sleeve to be positioned at a distal position in the shaft. The sleeve is then filled with uncured gas permeable polymeric material 118, such as silicone, to embed the optical fibers and guide ring in the shaft 119 of the multiple sensor. After the sensors are positioned, the polymeric material 118 is cured. The distal end of the sleeve is then scored at a point distal to the guide ring, as indicated by the arrows, so that the distal portion of the sleeve and matrix around the end of the optical fiber 116a can be exposed. As is shown in FIG. 8, the pH sensing module 114a is then applied to the distal end of the optical fiber 116a. Thereafter, the distal end portion 120 of the matrix is formed by application of the tipping matrix material at the distal end of the shaft, and formed into a rounded, hemodynamic shape, as shown in FIG. 9. The pH sensor may be covered by the tipping matrix material, or may project slightly from the distal end of the multiple sensor, as illustrated in FIGS. 6 and 9. The hydrophobic surfaces presented by the sleeve and the distal rounded end portion may be exposed to a high voltage corona discharge, and covered by a hydrophilic layer, as explained above, which may also cover a proximal portion of the pH sensor projecting from the distal end of the multiple sensor.

A further alternate embodiment of the multiple sensor showing a parabolic, or bullet shaped, rounded hemodynamic tip for the sensor is illustrated in FIG. 10. The multiple sensor 130 may, for example, have a generally cylindrical shaft 132 formed of hydrophobic semipermeable polymeric material such as a silicone which is molded, instead of utilizing a sleeve or semipermeable material for containing the optical fibers and matrix. An annular guide ring 131 is positioned transversely at the distal end 137 of the shaft, and includes a relatively narrow central aperture 135 for centrally locating the distal optical fiber pH sensor 134a on optical fiber 136a extending therethrough in the distal end portion 140. Blood gas sensors 94b and 94c are preferably axially staggered. A hydrophobic potting compound matrix 138, which is preferably silicone, substantially comprises the proximal portion 133 of the shaft.

A quantity of hydrophobic polymeric tipping compound matrix 138 is placed over the distal end of the shaft to form the rounded, hemodynamically shaped distal end 140. The pH sensor 134a extends through the guide ring to center the pH sensor in the distal portion of the hydrophobic potting compound matrix, projecting slightly from the rounded distal end portion of the hydrophobic potting compound matrix. The external hydrophobic surface of the shaft, the rounded distal end portion, and all or a portion of the projecting pH sensor may advantageously be covered by a layer of hydrophilic material 136, such as a hydrogel, cellulose, polyurethane, or the like, to provide a substantially continuous hydrophilic surface over the multiple sensor. The sleeve and distal hydrophobic portion of the potting matrix can advantageously both be prepared for bonding with the hydrophilic layer by exposure of the hydrophobic surfaces to a high voltage corona discharge. To enhance sensitivity, the amount of hydrophilic material covering the pH sensor is preferably no more than about 25 microns. An introducer catheter 144, guiding catheter, or the like may be used to insert the multiple sensor in the vasculature of a patient.

The external proximal surface 131 of the rounded distal end is parallel to and concurrent with the exterior surface layer 136 at the distal portion of the shaft 137, to maintain the overall hemodynamic shape of the multiple sensor. The external proximal surface of the rounded distal end is smoothly joined in this manner to the exterior surface of the shaft to reduce turbulence of blood flow around the distal end of the multiple sensor.

In a further alternate embodiment of the multiple sensor, the distal pH sensor may be disposed within the sleeve of the sensor, as shown in FIG. 11. The multiple sensor 150 may, for example, have a shaft 149 with a tubular sleeve 152 formed of a hydrophilic semipermeable polymeric material such as a cellulose, for containing the optical fibers and matrix. The distal optical fiber pH sensor 154a on optical fiber 156a extends to the distal end of the sleeve, and is preferably near to the surface of the shaft. Blood gas sensors 154b and 154c are preferably located proximal to the pH sensor, and are preferably axially staggered. A gas permeable hydrophilic potting compound matrix 158, which may be a gas permeable hydrogel, for example, substantially fills the proximal portion 153 of the shaft.

A hydrophilic polymeric tipping compound matrix 158 is preferably placed over the distal end of the shaft to form the rounded, hemodynamically shaped distal end 160, although the tip may also be formed of hydrophobic material, or even impermeable material. To enhance sensitivity, the amount of hydrophilic material covering the pH sensor is preferably no more than about 25 microns, for maximum sensitivity. An introducer catheter 164, guiding catheter, or the like may be used to insert the multiple sensor in the vasculature of a patient.

The external proximal surface 161 of the rounded distal end is parallel to and concurrent with the exterior surface layer 166 at the distal portion of the shaft 157, to maintain the overall hemodynamic shape of the multiple sensor. The external proximal surface of the rounded distal end is smoothly joined in this manner to the exterior surface of the shaft to reduce turbulence of blood flow around the distal end of the multiple sensor.

From the foregoing, it will be appreciated that the invention provides a multiple event sensor apparatus with individual sensors incorporated in a single tubular sleeve, resulting in a sensor assembly which is easily manufacturable and structurally sound. The axial staggering of the optical fiber sensors serves to minimize potential problems of cross-interference of the sensors, and allows the sleeve of the multiple sensor to be smoothly shaped so that in combination with the rounded tip, thrombus formation is minimized when the device is used intravascularly.

It will also be appreciated that the semipermeable, polymeric potting compound forms a continuous, semipermeable matrix having adjacent portions with different permeability characteristics appropriate for each component sensor disposed therein. The potting material provides structural integrity and strength for the multiple sensor, and maintains the individual optical fiber sensors in a fixed axially oriented position. The smoothly rounded, hemodynamically shaped distal end also provides a blood compatible, non-thrombogenic surface, allowing the multiple sensor apparatus to be positioned well within the bloodstream to avoid perturbations in the blood analyte measurements due to local analyte concentrations in the wall of a blood vessel. The central placement of the pH sensor in the distal, rounded end helps to prevent distortion of the hemodynamic shape of the distal end of the sensor. The rounded end also helps to avoid puncturing, or otherwise damaging, the blood vessel wall upon insertion of the multiple sensor.

While particular forms of the invention have been illustrated and described, it will be apparent that various modifications can be made without departing from the spirit and scope of this invention. Accordingly, it is not intended that the invention be limited, except as by the appended claims.

What is claimed is:

1. A multiple optical fiber sensor apparatus for intravascular use in measuring blood constituents, comprising:
   a semi-permeable shaft having proximal and distal ends and an exterior surface;
   a plurality of optical fibers extending longitudinally into said shaft, each of said optical fibers including a sensor module on a distal portion of said optical fiber, said sensor modules being disposed in axially staggered relationship, with at least one of said sensor modules comprising a gas sensor module disposed within a proximal portion of said shaft, and one of said sensor modules comprising a pH sensor module disposed distal to said gas sensor module;
   a semipermeable potting matrix disposed in said shaft, said potting matrix surrounding said optical fibers and at least a portion of said sensor modules for fixing the position of said sensor modules with respect to said shaft, each of said gas sensor modules being disposed in a gas permeable portion of said potting matrix and at least a portion of said pH sensor module being disposed in a hydrophilic portion of said potting matrix; and
   a rounded, hemodynamically shaped distal end portion adjoining said distal end of said shaft.

2. The apparatus of claim 1, wherein said rounded, hemodynamically shaped distal end portion has an exterior surface which is substantially parallel to and concurrent with the distal exterior surface of said shaft and is smoothly joined thereto, whereby said rounded distal end portion and said shaft are blood compatible and non thrombogenic.

3. The apparatus of claim 1, further including a gas permeable tubular sleeve having proximal and distal ends, with said semipermeable potting matrix substantially filling said sleeve.

4. The apparatus of claim 3, wherein said gas permeable sleeve is formed of hydrophobic material and is covered by an exterior layer of hydrophilic material.

5. The apparatus of claim 3, further including a guide member having an axial opening therethrough disposed within a distal portion of said sleeve.

6. The apparatus of claim 5, wherein said pH sensor module extends through said opening of said guide member.

7. The apparatus of claim 5, wherein said guide member comprises an annular guide ring disposed in the distal end of said tubular sleeve, and said annular guide ring and said tubular sleeve are formed together.

8. The apparatus of claim 5, wherein said guide member comprises an annular guide ring, and said guide ring is secured within the distal end of said tubular sleeve.

9. The apparatus of claim 8, wherein said rounded, hemodynamically shaped distal end portion is formed substantially from said gas permeable portion of said matrix and includes a concavity at a radially central location on the distal end of said end portion, at least a portion of said pH sensor module and at least a portion of said hydrophilic matrix portion being disposed in said concavity.

10. The apparatus of claim 9 wherein said tubular sleeve and said rounded distal end portion are formed of hydrophobic material and covered with a layer of hydrophilic material.

11. The apparatus of claim 3, further including a plug disposed within a distal portion of said sleeve, said plug having proximal and distal ends, with said distal end of said plug forming a substantial portion of the hemodynamically shaped, rounded distal end portion, and said plug having a generally longitudinal channel extending through said plug, through which said optical fiber for said pH sensor module extends.

12. The apparatus of claim 11, wherein said channel terminates in a concavity in a radially central portion of said rounded end portion, and at least a portion of said pH sensor module and at least a portion of said hydrophilic matrix portion are disposed in said concavity.

13. The apparatus of claim 11, wherein said plug is formed of hydrophobic material, and said tubular sleeve and said plug are covered with a layer of hydrophilic material.

14. The apparatus of claim 3, wherein said pH sensor module is disposed within said sleeve.

15. The apparatus of claim 14, wherein said distal end portion is formed of relatively impermeable material.

16. The apparatus of claim 1, wherein said shaft includes an exterior layer of hydrophilic material.

17. The apparatus of claim 16, wherein said layer of hydrophilic material is formed from a compound selected from the group consisting of hydrogel, cellulose, and combinations thereof.

18. The apparatus of claim 1, wherein said at least one gas sensor module comprises a blood oxygen sensor.

19. The apparatus of claim 1, wherein said at least one gas sensor module comprises a blood carbon dioxide sensor.

20. The apparatus of claim 1, wherein said at least one gas sensor module comprises a blood oxygen and a blood carbon dioxide sensor.

21. The apparatus of claim 1, wherein said semipermeable potting matrix is formed from a compound selected from the group consisting of silicone, hydrogel, polyurethane and combinations thereof.

22. The apparatus of claim 1, wherein said gas permeable portion of said matrix comprises a hydrophobic material.

23. The apparatus of claim 1, wherein said gas permeable portion of said matrix comprises a hydrophilic material.

24. The apparatus of claim 1, wherein said hemodynamically shaped rounded distal end is essentially hemispheric.

25. The apparatus of claim 1, wherein said hemodynamically shaped rounded distal end is essentially parabolic.

26. The apparatus of claim 1, wherein said hemodynamically shaped rounded distal end is in the shape of an ogive.

27. The apparatus of claim 1, wherein said pH sensor module projects slightly from said hemodynamically shaped, rounded distal end portion at a radially central location thereon.

28. The apparatus of claim 1, wherein said pH sensor module projects slightly from said hemodynamically shaped, rounded distal end at a location on said distal end portion at which stagnation of blood flow normally occurs when said apparatus is disposed intravascularly.

29. An intravascular multiple sensor apparatus, comprising:
a gas permeable, generally cylindrical shaft having proximal and distal ends;
a plurality of optical fibers having proximal and distal ends and extending longitudinally within said shaft, the distal portion of each said optical fiber having a sensor module, at least one of said sensor modules being a gas sensor module disposed within said shaft, and one other of said sensor modules being a pH sensor module;
a gas permeable polymeric matrix portion having proximal and distal end disposed within said shaft, said gas permeable polymeric matrix surrounding said gas sensor modules and fixing the position of said optical fibers with respect to said shaft;
a hydrophilic polymeric matrix portion disposed within said shaft, said hydrophilic polymeric matrix portion surrounding said pH sensor module; and
a hemodynamically shaped, rounded distal end portion adjoining said distal end of said shaft, said end portion having an exterior surface which is substantially parallel to and concurrent with the distal exterior surface of said shaft, and smoothly joined thereto.

30. The apparatus of claim 29, wherein said shaft is covered with a layer of hydrophilic material.

31. The apparatus of claim 30, wherein said layer of hydrophilic material is formed from a compound selected from the group consisting of hydrogel, cellulose, and combinations thereof.

32. The apparatus of claim 29, wherein said shaft includes a gas permeable tubular member having proximal and distal ends, and said tubular member contains said gas permeable polymeric matrix and at least one gas sensor module.

33. The apparatus of claim 32, further including a guide member having a central opening therethrough within the distal end of said tubular member, with said optical fiber terminating in a pH sensor module extending through said central opening.

34. The apparatus of claim 33, wherein said guide member comprises an annular guide ring disposed in the distal end of said tubular member, and said annular guide ring and said tubular member are formed unitarily.

35. The apparatus of claim 34, wherein said hemodynamically shaped, rounded distal end portion is formed substantially from said gas permeable matrix portion and includes a central concavity at the distal end of said end portion in which said pH sensor module and at least a portion of said hydrophilic matrix portion are disposed.

36. The apparatus of claim 33, wherein said guide member comprises an annular guide ring disposed in the distal end of said tubular member, and said annular guide ring and said tubular member are bonded together.

37. The apparatus of claim 36, wherein said hemodynamically shaped, rounded distal end portion is formed substantially from said gas permeable matrix portion and includes a radially central concavity at the distal end of said end portion in which said pH sensor module and at least a portion of said hydrophilic matrix portion are disposed.

38. The apparatus of claim 37, wherein said tubular member and said gas permeable portion of said rounded distal end portion are formed of hydrophobic material, and are covered with a layer of hydrophilic material formed from a compound selected from the group consisting of hydrogel, cellulose, and combinations thereof.

39. The apparatus of claim 33, wherein said guide member comprises a generally cylindrical plug having proximal and distal ends, with said distal end of said tubular plug forming a substantial portion o the hemodynamically shaped, rounded distal end portion, said central opening comprising a channel extending from said proximal end of said plug to terminate in a central concavity at the distal end of said plug in which said pH sensor module and at least a portion of said hydrophilic matrix portion are disposed.

40. The apparatus of claim 39, wherein said tubular member and said plug are formed of hydrophobic material, and are covered with a layer of hydrophilic material formed from a compound selected from the group consisting of hydrogel, cellulose, and combinations thereof.

41. The apparatus of claim 32, wherein said pH sensor module is disposed within said tubular member.

42. The apparatus of claim 29 wherein one of said gas sensor modules comprises a blood oxygen sensor.

43. The apparatus of claim 29, wherein said gas permeable polymeric matrix is formed from a compound selected from the group consisting of silicone, hydrogel, polyurethane, and combinations thereof.

44. The apparatus of claim 29, wherein said at least one gas sensor module comprises a blood carbon dioxide sensor.

45. The apparatus of claim 29, wherein said at least one gas sensor module comprises a blood oxygen sensor and a blood carbon dioxide sensor.

46. The apparatus of claim 29, further comprising sensor means to sense a physiologic parameter of a patient.

47. The apparatus of claim 46 wherein said sensor means comprises means to sense temperature.

48. The apparatus of claim 46 wherein said sensor means comprises means to sense blood pressure.

49. The apparatus of claim 29, wherein said hemodynamically shaped rounded distal end is in the shape of a hemisphere.

50. The apparatus of claim 29, wherein said hemodynamically shaped rounded distal end has a parabolic shape.

51. The apparatus of claim 29, wherein said hemodynamically shaped rounded distal end is in the shape of an ogive.

52. The apparatus of claim 29, wherein said pH sensor projects slightly from said hemodynamically shaped, rounded distal end portion at a radially central location thereon at which stagnation of blood flow normally occurs when said apparatus is disposed intravascularly.

53. A method for manufacturing an intravascular multiple optical fiber sensor having a generally longitudinal semi-permeable shaft, a plurality of optical fibers having proximal and distal ends extending longitudinally through said shaft and terminating at their distal ends in a sensor module, with at least one of said sensor modules comprising a gas sensor module and one of said sensor modules comprising a pH sensor module, a semi-permeable potting matrix disposed in said shaft with a gas permeable portion of said matrix surrounding said gas sensor modules and a hydrophilic portion of said potting matrix surrounding at least a portion of said pH sensor module, and a rounded, hemodynamically shaped distal end portion adjoining a distal end of said shaft, comprising the steps of:

axially staggering the distal ends of a bundle of said optical fibers, with at least one optical fiber gas sensor module being disposed proximally and said optical fiber for the pH sensor module extending most distally;

locating said distally located pH sensor module in a radially central position with respect to the distal end of said multiple sensor;

surrounding said optical fibers with uncured gas permeable polymeric material and curing said gas permeable polymeric material to form said shaft;

forming said generally rounded distal end portion of said multiple sensor; and covering at least a portion of said pH sensor module with hydrophilic material to complete the hemodynamic shape of said distal end portion.

54. The method of claim 53, wherein said step of locating said pH sensor module optical fiber comprises positioning a guide member having a central opening therethrough at a distal position relative to said gas sensor modules, and inserting said pH sensor module optical fiber through said guide member.

55. The method of claim 53, wherein said optical fibers are introduced into a tubular member having proximal and distal ends, and an annular guide ring is placed transversely in the distal end of the tubular member for radially centering the distal pH sensor module with the hemodynamically rounded distal end of the multiple sensor.

56. The method of claim 55, wherein said tubular member is formed of gas permeable hydrophobic material, and further comprising the steps of subjecting the exterior surface of said tubular member to a high voltage corona discharge, and covering said tubular member with a layer of hydrophilic material to provide the shaft of said multiple sensor with hydrophilic surface characteristics.

57. The method of claim 55, wherein said tubular member and said distal end portion of said multiple sensor are formed of hydrophobic material, and further comprising the steps of subjecting the exterior surface of said tubular member and said distal end portion of said multiple sensor to a high voltage corona discharge, and covering the hydrophobic surfaces of said tubular member and said distal end portion of said multiple sensor with a layer of hydrophilic material to provide said multiple sensor with hydrophilic surface characteristics.

* * * * *

UNITED STATES PATENT AND TRADEMARK OFFICE
CERTIFICATE OF CORRECTION

PATENT NO. : 5,166,990

DATED : November 24, 1992

INVENTOR(S) : Samuel D. Riccitelli, et al.

It is certified that error appears in the above-identified patent and that said Letters Patent is hereby corrected as shown below:

Column 2, line 54, delete "On" and insert therefor --One--.

Column 4, line 9, delete "non thrombogenic" and insert therefor --non-thrombogenic--

Column 5, line 52, delete "showning" and insert therefor --showing--

Column 6, line 42, delete "assets" and insert therefor --assists--

Column 7, line 14, delete "may"

Column 7, line 68, delete "in the sensor" and insert --.-- therefor after the word "used"

Column 8, line 1, following the word "included" insert --in the sensor--

Column 8, line 17, delete "nonthrombogenic" and insert therefor --non-thrombogenic--

Column 9, line 23, delete "." following the word "be"

Column 9, line 54, delete "nonthrombogenic" and insert therefor --non-thrombogenic--

UNITED STATES PATENT AND TRADEMARK OFFICE
CERTIFICATE OF CORRECTION

PATENT NO. : 5,166,990

DATED : November 24, 1992

INVENTOR(S) : Samuel D. Riccitelli, et al.

It is certified that error appears in the above-identified patent and that said Letters Patent is hereby corrected as shown below:

Column 16, lines 24 and 25 (Claim 2, line 7), delete "non thrombogenic" and insert therefor --non-thrombogenic--

Column 17, line 23 (Claim 20, line 2), insert --sensor-- following the word "oxygen"

Column 18, line 20 (Claim 32, line 4), delete "g as" and insert therefor --gas--

Column 18, line 60 (Claim 39, line 4), delete "o" and insert therefor --of--

Column 19, line 7 (Claim 42, line 1), following the number "29" insert --,--

Column 19, line 22 (Claim 47, line 1), following the number "46" insert --,--

Column 19, line 24 (Claim 48, line 1), following the number "46" insert --,--

Signed and Sealed this

Twenty-fifth Day of January, 1994

*Attest:*

BRUCE LEHMAN

*Attesting Officer*    Commissioner of Patents and Trademarks